United States Patent [19]

Ota et al.

[11] Patent Number: 5,230,903

[45] Date of Patent: Jul. 27, 1993

[54] CHLOROISOCYANURATE COMPOSITION

[75] Inventors: Masanori Ota; Masashi Nakamura; Kenichi Mizusawa, all of Funabashi, Japan

[73] Assignee: Nissan Chemical Industries, Ltd., Tokyo, Japan

[21] Appl. No.: 802,710

[22] Filed: Dec. 6, 1991

Related U.S. Application Data

[63] Continuation of Ser. No. 343,690, Apr. 27, 1989, abandoned.

[51] Int. Cl.⁵ .................... A01N 59/06; A01N 43/66
[52] U.S. Cl. .................... 424/692; 514/241; 514/970
[58] Field of Search ............... 424/692, 693; 514/241, 514/970; 252/186.35

[56] References Cited

U.S. PATENT DOCUMENTS

| | | | |
|---|---|---|---|
| 3,457,167 | 7/1969 | Spiegel et al. | 514/241 |
| 3,899,436 | 8/1975 | Copeland et al. | 252/99 |
| 4,279,764 | 7/1981 | Brubaker | 252/99 |
| 4,334,618 | 6/1982 | Ota et al. | 252/186.35 |
| 4,472,187 | 9/1984 | Wojtowicz | 71/67 |
| 4,498,921 | 2/1985 | Wojtowicz | 71/67 |
| 5,021,186 | 6/1991 | Ota et al. | 252/186.35 |

FOREIGN PATENT DOCUMENTS

| | | |
|---|---|---|
| 0105952 | 4/1984 | European Pat. Off. |
| 2178220 | 3/1973 | France . |
| 59-67208 | 4/1984 | Japan . |
| 192800 | 8/1986 | Japan .................. 252/99 |

OTHER PUBLICATIONS

Chemical Abstracts, vol. 105 (1986), 228974t.
Chemical Abstracts, vol. 94 (1981), 30802w.
Chemical Patents Index, Basic Abstracts Journal, Week D51, Section C, Abstract No. 93758 (Feb. 17, 1982).
Chemical Patents Index, Basic Abstracts Journal, Week 8504, Section C, Abstract No. 22827 (Mar. 20, 1985).
Chemical Patents Index, Basic Abstracts Journal, Week 8821, Section A, Abstract No. 145113 (Jul. 20, 1988).

*Primary Examiner*—Frederick E. Waddell
*Assistant Examiner*—K. Weddington
*Attorney, Agent, or Firm*—Oliff & Berridge

[57] ABSTRACT

Chloroisocyanurate compositions for disinfection and sterilization comprise a dichloroisocynurate and at least one alkaline substance selected from the group consisting of magnesium oxide, magnesium hydroxide, calcium hydroxide and sodium carbonate. The chloroisocyanurate compositions can prevent an increase in hydrogen ion concentration often caused by continuous use of dichloroisocyanurates in closed water systems and have excellent stability in a wet state and stability during storage over long periods of time.

4 Claims, No Drawings

CHLOROISOCYANURATE COMPOSITION

This is a continuation of application Ser. No. 07/343,690 filed Apr. 27, 1989, now abandoned.

BACKGROUND OF THE INVENTION

1. Field of the Invention

The present invention relates to a chloroisocyanurate composition for disinfection and sterilization, more particularly, to a composition comprising a dichloroisocyanurate, which may be used to prevent an increase in hydrogen ion concentration and which has excellent stability during storage.

2. Decription of the Prior Art

Dichloroisocyanurates have been widely used due to the fact that since active chlorine (residual chlorine) supplied in water is stable as compared to a sodium hypochlorite solution or highly bleaching powders (main ingredient: calcium hypochlorite) and thus only a small amount is required, they are free from calcium hydroxide or calcium carbonate as in highly bleaching powders, and they are completely soluble and have a potent bactericidal activity. For example, bactericidal disinfectants or slime controlling agents for sewage, pool water, cooling water, etc. in the form of powder granular, tablet, etc. preparations.

However, in the case that dichloroisocyanurates are supplied continuously or intermittently over long periods of time for sterilization, disinfection or slime control of water which is in a closed system, for example, cooling water, pool water, etc., dichloroisocyanurates accumulate in reservoir water frequently causing an increase in hydrogen ion concentration in the water. This tendency is particularly significant in water having low alkalinity, such as rain water. Furthermore, in water such as cooling water which is recycled over long periods of time and relatively easily polluted, the amount of dichloroisocyanurates to be supplied is increased so that the hydrogen ion concentration in the water also increases. When the hydrogen ion concentration increases, corrosion of equipment, etc. occurs.

For these reasons, a method of periodically sprinkling sodium carbonate has been adopted to prevent such an increase in hydrogen ion concentration in water in a closed system. However, supplying sodium carbonate while measuring pH and controlling the amount of sodium carbonate is complicated.

Extensive studies have not been made as to how to prevent an increase of the hydrogen ion concentration due to continuous use of dichloroisocyanurates in a closed water system as described above. A method has been proposed in Japanese Patent Laid-open Publication No. Sho 59-67208 (67208/1984) in which isocyanuric acid and magnesium oxide or magnesium hydroxide are formulated in trichloroisocyanuric acid. However, when using this method in a closed water system over long periods of time, the pH of the water may gradually decrease. Furthermore, there has been proposed a trichloroisocyanuric acid composition having formulated therein an alkaline substance. However, this composition is unstable when in a moistened state (wet state), such that it generates nitrogen chloride gas having explosive properties. That is, care must be taken when handling the composition and during storage of the composition, wetting should be strictly prohibited.

SUMMARY OF THE INVENTION

In order to prevent the increase of hydrogen ion concentration caused by continuous use of dichloroisocyanurate compounds in a closed water system and to obtain a composition having good stability during storage, the present inventors have made extensive studies on sensitive physical properties of the dichloroisocyanurates described and the mechanism for forming nitrogen chloride. As a result, it has been surprisingly found that by providing a specific alkaline substance in a specific ratio, the dichloroisocyanurates can be extremely stably formulated.

That is, the present invention relates to a chloroisocyanurate composition comprising (1) 10 to 60 parts by weight of at least one alkaline substance selected from the group consisting of magnesium oxide, magnesium hydroxide, calcium hydroxide and sodium carbonate, and (2) 100 parts by weight of a dichloroisocyanurate.

DETAILED DESCRIPTION OF THE PREFERRED EMBODIMENTS

The dichloroisocyanurate according to the present invention includes anhydride or dihydrate of sodium dichloroisocyanurate, potassium dichloroisocyanurate and the like, which may also be used in combination. The at least one alkaline substance selected from magnesium oxide, magnesium hydroxide, calcium hydroxide and sodium carbonate is provided in an amount of from 10 to 60 parts by weight, preferably 15 to 50 parts by weight, based on 100 parts by weight of the dichloroisocyanurate. When the amount of the alkaline substance is less than 10 parts by weight, there is a tendency for its hydrogen ion concentration to increase and for its pH value to decrease, when used in a closed water system over long periods of time. On the other hand, when the amount exceeds 60 parts by weight, the stability of the composition when in a wet state decreases and noxious nitrogen chloride gas tends to generate. Furthermore, when using other alkaline substances such as calcium oxide, sodium orthoborate, sodium metasilicate, sodium hydroxide, etc., the stability of the dichloroisocyanurate composition is poor when in a wet state and such alkaline substances cannot be used.

The process for producing the dichloroisocyanurate composition according to the present invention is not particularly limited, for example, dry mixing with a V-shaped mixer, a ribbon mixer, etc. which are conventionally used may be applied.

The composition of the present invention can be used in optional forms such as powders, granules, pills, tablets, etc. Taking handling into account, granules or tablets are preferred. When granulating, better results can be obtained by using components for formulation having a particle size of 500μ (micron) or less. When the particle size exceeds 500μ, molding tends to be non-uniform and stability of the molding when in a wet state is reduced.

For forming granules, there are (1) a conventional method for dry granulation which comprises press molding into a sheet using a 2-roll mill, crushing into granules and classifying, and (2) a method for wet granulation which comprises granulating a wet-cake into cylindrical particles with an extending granulator or further applying the granules to a rolling granulator or a spherical particle dresser into spherical granules. In a method for preparing tablets, it is preferred that the granules obtained by the methods described above be tableted.

Upon granulation, if necessary, an excipient such as a binder, fluidizing agent, lubricant, etc. and an auxiliary agent such as a disintegrating agent, etc. may be incorporated. Furthermore, a filler may also be incorporated to appropriately control the concentration.

The chloroisocyanurate composition obtained in the present invention can be stored over long period of time, can minimize the generation of nitrogen chloride when in a wet state and provides increased safety. Even when the dichloroisocyanurate composition is used over long periods of time in a closed water system such as indoor heated swimming pool, etc., hydrogen ion concentration does not increase, i.e., there is no reduction in pH.

As described above, the composition according to the present invention can prevent an increase in the hydrogen ion concentration even in the case of continuously supplying the chloroisocyanurate into a reservoir tank in a closed system over long periods of time. Moreover, the composition can be stored stably.

Hereafter the present invention is described in detail by referring to the examples and comparative examples but the technical scope of the present invention should not be construed as being limited thereto.

EXAMPLES

Example 1

To 1 kg of anhydride of sodium dichloroisocyanurate having a particle size of 50 to 350μ and a moisture content of 0.14 % was added 180 g of magnesium oxide having a particle size of 100μ or less and a moisture content of 0.11 %. The mixture was granulated with a compacting machine. After crushing, classification was performed to give granules having particle size of 10 mesh screen pass and 32 mesh screen stop.

Tableting was effected by a method in which the granules granulated with the compacting machine were charged into a mold having a 25 mm diameter cavity followed by continuous tableting with a rotary tableting machine under a compression pressure of about 400 kg/cm$^2$ Thus, a cylindrical tablet having a diameter of 25 mm, a thickness of 13 mm and a weight of 10 g was prepared.

The granules were used for evaluating the hydrogen ion concentration and a tablet weighing 10 g was used to evaluate stability in a wet state.

(A) Evaluation of Hydrogen Ion Concentration

In a beaker was charged 1 liter of water having Methyl Orange alkalinity of 5 mg/l (adjusted by mixing tap water with distilled water) calculated as $CaCO_3$. Granules of the chloroisocyanurate composition were put into the beaker in an amount sufficient to produce residual chlorine concentration of 60 mg/l in the water, and the granules were stirred and dissolved. A low temperature type ultraviolet ray lamp (wavelength of 250 to 3000 Å) of 10 W was immersed in the water in the beaker. When ultraviolet rays were irradiated to the water over about 6 hours, the residual chlorine completely disappeared over about 6 hours; pH at this time was measured.

The residual chlorine concentration of 2 mg/l corresponds to a mean daily amount used in an actual pool and 60 mg/l corresponds to an amount used for 30 days. That is, the measurement in the residual chlorine concentration of 60 mg/l is used to simulate measurement of pH in pool water after 30 days.

(B) Evaluation of Stability

In an Erlenmeyer's flask having an inner volume of 300 ml was charged 10 g of the chloroisocyanurate tablet. Then, 10 ml of water was poured onto the surface of the tablet and the flask was stoppered. After the flask was allowed to settle for 5 minutes at 35° C., the stopper was opened. The gas generated by decomposition was examined by an organoleptic test. The results are shown in Tables 1 and 2.

Examples 2 through 11, Reference Examples 1 through 3 and Comparative Examples 1 through 10

Granules or tablets were prepared by formulating compositions shown in Tables 1 and 2 in a manner similar to Example 1. Evaluation was made in a manner similar to Example 1. Particle sizes of the raw materials for the formulated compositions were the same as those in Example 1 except in Comparative Example 10, in which the particle size of sodium dichloroisocyanurate anhydride was from 750 to 1500μ.

The results are shown in Tables 1 and 2. As shown in Tables 1 and 2, the chloroisocyanurate compositions of the present invention show substantially no change in pH and exhibit excellent stability in a wet state.

In the tables, "Ex." means Example; "Ref. Ex." means Reference Example; and "Comp. Ex." means Comparative Example.

TABLE 1

| | Formulation Composition (per 100 parts by weight of Chloroisocyanurate) | | | | Results of Evaluation | |
|---|---|---|---|---|---|---|
| | Chloroiso-cyanurate | Alkaline compound | Disintegrating agent | Lubricant | Change in pH | Wet stability |
| Ex. 1 | DCCNa*1 | Magnesium oxide 18 | — | — | 6.87 → 6.74 | ⊚ |
| Ex. 2 | " | Magnesium oxide 25 | — | — | — | ⊚ |
| Ex. 3 | " | Magnesium oxide 25 | — | 0.2*5 | — | ⊚ |
| Ex. 4 | " | Magnesium hydroxide 25 | — | — | — | ⊚ |
| Ex. 5 | " | Sodium carbonate 44 | 3.0*4 | — | 6.84 → 6.91 | ○ |
| Ex. 6 | " | Sodium carbonate 44 | " | 0.2*5 | — | ○ |
| Ex. 7 | DCCNa 2H$_2$O*2 | Magnesium hydroxide 25 | " | " | 6.91 → 6.87 | |
| Ex. 8 | DCCNa 2H$_2$O*2 | Sodium carbonate 44 | " | " | — | ○ |

TABLE 1-continued

| | Formulation Composition (per 100 parts by weight of Chloroisocyanurate) | | | | Results of Evaluation | |
|---|---|---|---|---|---|---|
| | Chloroiso-cyanurate | Alkaline compound | Disintegrating agent | Lubricant | Change in pH | Wet stability |
| Ex. 9 | DCCK*3 | Calcium hydroxide 25 | — | — | 6.80 → 6.84 | ○ |
| Ex. 10 | " | Magnesium oxide 18 | — | — | — | ⊙ |
| Ref. Ex. 1 | DCCNa | — | — | — | 6.78 → 5.11 | ⊙ |
| Ref. Ex. 2 | DCCNa.2H₂O | — | — | — | 6.82 → 5.07 | ⊙ |
| Ref. Ex. 3 | DCCK | — | — | — | 6.96 → 4.92 | ⊙ |

*¹DCCNa: sodium dichloroisocyanurate anhydride
*²DCCNa.2H₂O: dichloroisocyanurate dihydrate
*³DCCK: potassium dichloroisocyanurate
*⁴disintegrating agent: carboxymethyl cellulose Ca
*⁵lubricant: sodium stearate

TABLE 2

| | Formulation Composition (per 100 parts by weight of Chloroisocyanurate) | | | | Results of Evaluation | |
|---|---|---|---|---|---|---|
| | Chloroiso-cyanurate | Alkaline compound | Disintegrating agent | Lubricant | Change in pH | Wet stability |
| Comp. Ex. 1 | DCCNa | Calcium oxide 25 | — | — | — | X |
| Comp. Ex. 2 | DCCNa.2H₂O | Sodium orthophosphate 40 | — | — | — | Δ |
| Comp. Ex. 3 | DCCK | Sodium meta-silicate 40 | — | — | — | Δ |
| Comp. Ex. 4 | DCCNa | Sodium hydroxide 70 | — | — | — | X |
| Comp. Ex. 5 | " | Magnesium oxide 70 | — | — | — | Δ |
| Comp. Ex. 6 | " | Magnesium hydroxide 70 | — | — | — | Δ |
| Comp. Ex. 7 | " | Sodium carbonate 70 | — | — | — | Δ |
| Comp. Ex. 8 | " | Magnesium oxide 9 | — | — | 6.84 → 6.05 | ⊙ |
| Comp. Ex. 9 | " | Sodium carbonate 9 | — | — | 6.88 → 5.70 | ⊙ |
| Comp. Ex. 10 | " | Sodium carbonate 25 | — | — | — | Δ |

⊙ After the opening of the stopper, irritant odor is remarkably weak or there is little odor.
○ After the opening of the stopper, there is weak irritant odor.
Δ After the opening of the stopper, there is remarkable irritant odor though the inside of the flask is not turned yellow.
X During storage, decomposition gas remarkably generates and the inside of the flask is turned yellow.

While the present invention has been described in detail and with reference to specific embodiments thereof, it will be apparent to one skilled in the art that various changes and modifications can be made therein without departing from the spirit and scope thereof.

What is claimed is:

1. A chloroisocyanurate composition, comprising (1) 10 to 60 parts by weight of at least one compound selected from the group consisting of magnesium oxide and magnesium hydroxide and (2) 100 parts by weight of at least one compound selected from the group consisting of anhydride of sodium dichloroisocyanurate, dihydrate of sodium dichloroisocyanurate and potassium dichloroisocyanurate.

2. A chloroisocyanurate composition as claimed in claim 1, wherein said chlorisocyanurate composition comprises at least one granule formed from powdery raw formulation materials having an average particle size of not greater than 500μ.

3. A chloroisocyanurate composition as claimed in claim 1, wherein said chloroisocyanurate composition comprises at least one tablet obtained by powdery raw formulation materials having an average particle size of not greater than 500μ.

4. A method for disinfecting and sterilizing water in a closed system, comprising adding to said water a chloroisocyanurate composition comprising (1) 10 to 60 parts by weight of at least one compound selected from the group consisting of magnesium oxide and magnesium hydroxide and (2) 100 parts by weight of at least one compound selected from the group consisting of anhydride of sodium dichloroisocyanurate, dihydrate of sodium dichloroisocyanurate and potassium dichloroisocyanurate.

* * * * *